(12) United States Patent  
Nadolski

(10) Patent No.: US 7,483,607 B2
(45) Date of Patent: Jan. 27, 2009

(54) DUAL CORE OPTIC FIBER ILLUMINATED LASER PROBE

(75) Inventor: Timothy John Nadolski, Webster Groves, MO (US)

(73) Assignee: Synergetics, Inc., O'Fallon, MO (US)

( * ) Notice: Subject to any disclaimer, the term of this patent is extended or adjusted under 35 U.S.C. 154(b) by 0 days.

(21) Appl. No.: 11/558,738

(22) Filed: Nov. 10, 2006

(65) Prior Publication Data

US 2008/0107384 A1    May 8, 2008

Related U.S. Application Data

(63) Continuation-in-part of application No. 11/557,264, filed on Nov. 7, 2006.

(51) Int. Cl.
*G02B 6/04* (2006.01)
*G02B 6/06* (2006.01)

(52) U.S. Cl. .................. 385/115; 385/116; 385/117; 385/118; 385/119

(58) Field of Classification Search ......... 385/115–119, 385/126, 127
See application file for complete search history.

(56) References Cited

U.S. PATENT DOCUMENTS 5,328,365 A * 7/1994 Jacoby ..................... 433/29
2007/0122096 A1* 5/2007 Temelkuran et al. ........ 385/126

* cited by examiner

*Primary Examiner*—Frank G Font
*Assistant Examiner*—Jerry Blevins
(74) *Attorney, Agent, or Firm*—Thompson Coburn LLP

(57) ABSTRACT

A microsurgical laser probe primarily used in ophthalmic surgery provides both laser light and illumination light to a surgical site from a single light source. The laser probe has a dual core optic fiber that transmits both laser light and illumination light to the surgical site. A center core of the optic fiber transmits the laser light through the optic fiber and emits the laser light at the surgical site. The center core of the fiber is surrounded by an outer fiber core. The outer fiber core transmits illumination light through the optic fiber and emits the illumination light at the surgical site.

31 Claims, 3 Drawing Sheets

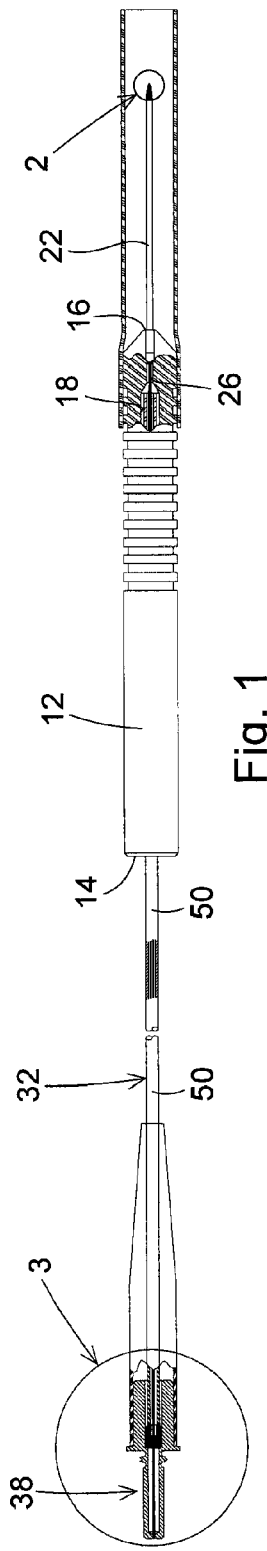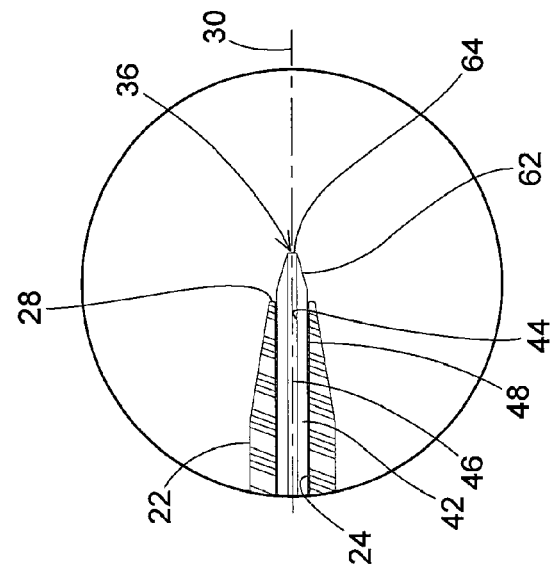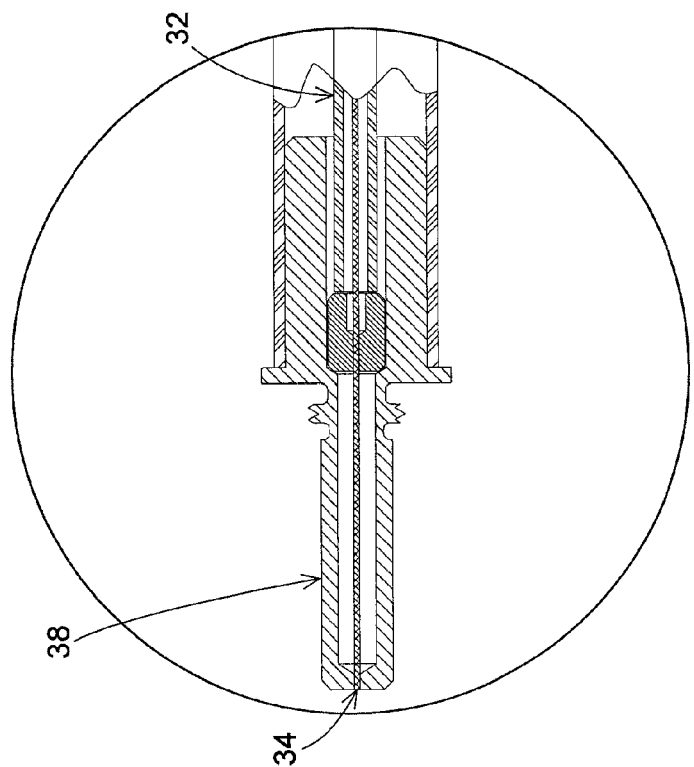
Fig. 1
Fig. 2
Fig. 3

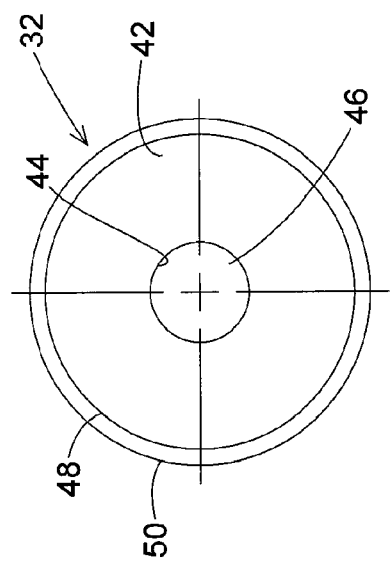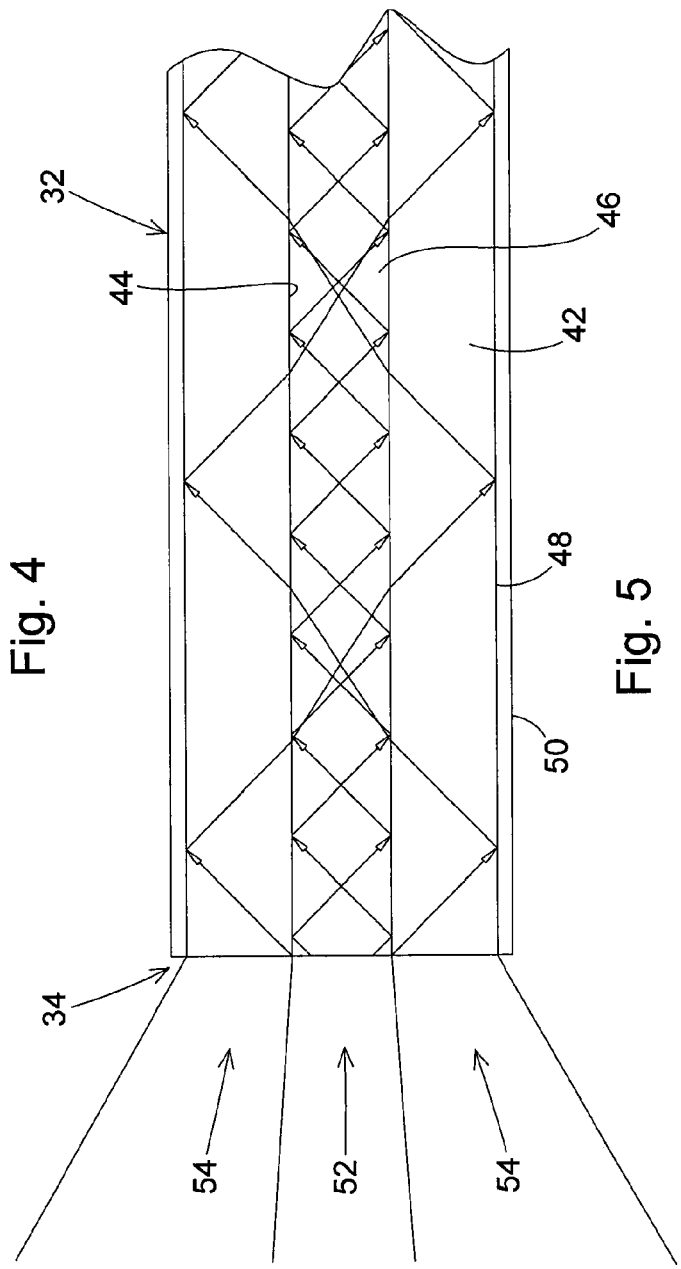

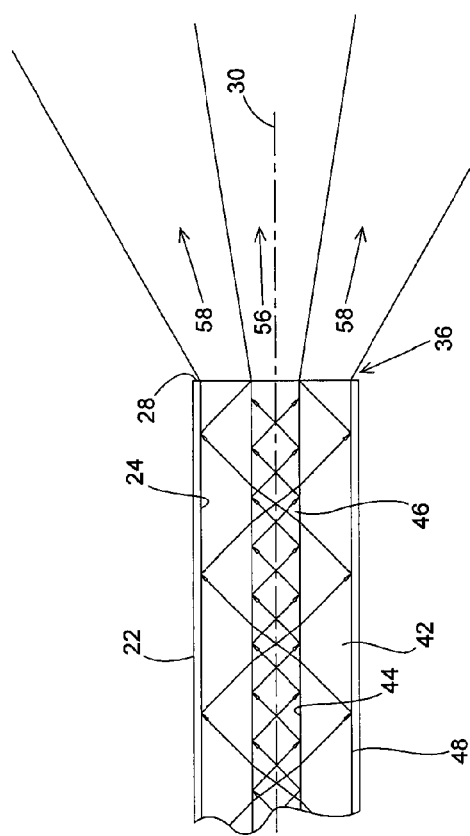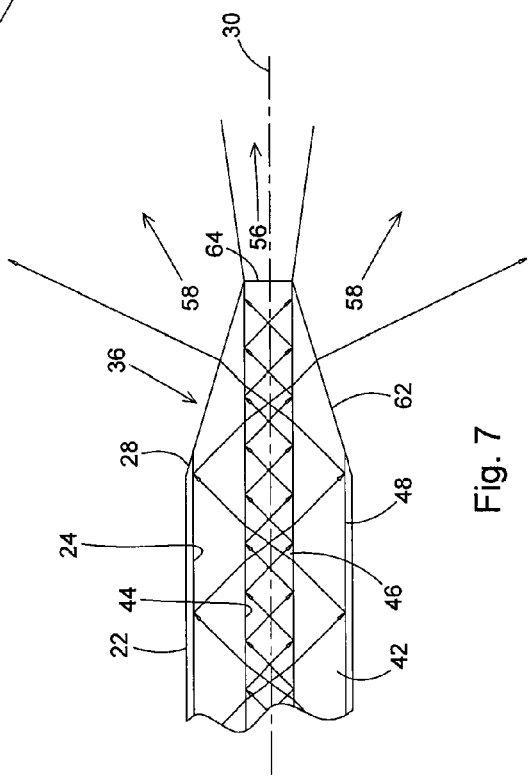

DUAL CORE OPTIC FIBER ILLUMINATED LASER PROBE

This application is a continuation-in-part of patent application Ser. No. 11/557,264, which was filed on Nov. 7, 2006, and is currently pending.

BACKGROUND OF THE INVENTION (1) Field of the Invention

The present invention pertains to a microsurgical laser probe used primarily in ophthalmic surgery where the probe provides both laser light and illumination light to a surgical site. More specifically, the laser probe of the invention has a dual core optic fiber that transmits both laser light and illumination light to a surgical site. A center core of the optic fiber transmits the laser light through the fiber and emits the laser light at the surgical site. The center core of the fiber is surrounded by an outer fiber core. The outer core transmits illumination light through the fiber and emits the illumination light at the surgical site.

(2) Description of the Related Art

Laser endoprobes or microsurgical probes and white light illumination probes have been employed in performing ophthalmic surgery procedures for many years. Until the early 1980's, laser probes and illumination probes were separate and independent instruments. Examples of these are disclosed in the U.S. Pat. No. 7,060,028 and U.S. Pat. No. 4,607,622.

In 1986, the Mir Ali U.S. Pat. No. 4,583,526 disclosed a handpiece that had a carbon dioxide laser and an illumination light source traveling in parallel. The U.S. patents of Easley et al. U.S. Pat. No. 5,275,593 and U.S. Pat. No. 5,356,407 also disclose instruments that combined both laser and illumination fibers in the same probe. Presently, almost all of the major ophthalmic surgery instrument manufacturing companies have a line of illuminated laser probes. These probes work on the basic premise that two or more fibers are fed down the length of a tubular tip at the front of an instrument. The distal ends of the fibers are positioned adjacent to the distal end of the tip. The proximal end of one of the fibers is connected to a laser light source, and the proximal end of the other fiber is connected to an illumination light source.

As ophthalmic illumination sources have improved, the size and the number of optic fibers that are used in microsurgical instruments has decreased. In 2004, Synergetics, Inc. developed a light source capable of coaxially aligning a laser light and a white light illumination path so that both would be able to travel down a single fiber. This allowed for the use of a single optic fiber that would simultaneously provide both illumination light and laser light at the surgical site.

However, there were problems associated with using a single optic fiber for the transmission of both illumination light and laser light to the surgical site. It was observed that the light emitted from the optic fiber distal end would have the same divergence angle as the light delivered by the light source to the optic fiber proximal end. This meant that the area of illumination at the surgical site would be directly proportional to the size of the laser light spot at the surgical site. For example, the illumination light divergence angle at the distal end of the optic fiber would normally be 30 degrees off the center axis, and the laser light divergence angle at the distal end of the optic fiber would normally be 8 degrees off the axis. When the microsurgical probe distal end tip would be positioned close enough to the surgical site to get a laser light spot sized small enough for a desired burn, the area of illumination would be very small.

Illuminated laser probes have been designed according to two methods to compensate for this shortcoming. Probes have been designed with two staggered optic fibers, with the distal end of the illumination optic fiber being spaced back from the distal end of the laser optic fiber. This design would provide a larger area of illumination at the surgical site, but would produce a shadow in the illumination area where the illumination light is blocked by the distal end of the laser optic fiber. The other solution was to make the illumination optic fiber a wide field fiber. This was done through the use of a cone-shaped lens such as that disclosed in the U.S. Pat. No. 6,829,411, or the use of optical films, or an emulsion of glass spheres or balls. However, each of these would also produce a shadow of the laser optic fiber. Furthermore, the single optic fiber design would not allow for any of these options because it would scatter all of the illumination light and laser light transmitted equally.

SUMMARY OF THE INVENTION

The surgical instrument of the invention provides both illumination light and laser light in laser eye surgery. The instrument is basically comprised of an elongate handle, an elongate tubular tip projecting from the handle, and a dual core optic fiber that extends through the handle and the tip.

The dual core optic fiber has an elongate length with opposite proximal and distal ends. A distal end portion of the optic fiber extends through the handle and the tip. In alternate embodiments of the instrument, the fiber is secured stationary to the handle and the tip, or is capable of moving through the handle and the tip.

A laser light source connector is provided at the fiber proximal end. The connector is adapted for connecting the optic fiber proximal end to a separate light source. The light received by the optic fiber proximal end travels through the length of the optic fiber and is emitted from the optic fiber distal end.

A novel feature of the invention is provided by the dual core construction of the optic fiber. The optic fiber has a center core that extends the entire length of the fiber. An outer core surrounds the center core and also extends from the optic fiber proximal end to the optic fiber distal end. A cladding layer surrounds the outer core and extends the length of the optic fiber. A buffer layer surrounds the cladding layer and extends a majority of the length of the optic fiber. The two cores of the optic fiber are made from silica glass, or an equivalent material, and each have a different index of refraction. In the dual core optic fiber, the outer core functions as an illumination optic fiber that transmits illuminating light, and the inner core functions as a laser optic fiber that transmits laser light. The index of refraction of the inner optic fiber is larger than the index of refraction of the outer optic fiber. The cladding layer has a lower index of refraction than that of the dual cores of the optic fiber.

The center core of the optic fiber will emit light at both narrow and wide divergence angles. This happens because the wider angle light rays refract through the center core along the length of the optic fiber. The outer core will also emit narrow and wide angle light. The inner core will maintain a narrow divergence angle light that impinges on its proximal end. Thus, with the connector at the optic fiber proximal end connected to a laser light source, laser light focused only on the center core will be emitted from the center core at the optic fiber distal end. Illumination light will be transmitted by the outer optic fiber and be emitted from the outer core at the optic fiber distal end.

BRIEF DESCRIPTION OF THE DRAWINGS

The dual core fiber optic laser probe of the invention overcomes the disadvantages of prior art illuminated laser probes. The features of the invention that overcome the shortcomings of the prior art are set forth in the following detailed description of the preferred embodiments of the invention and in the drawing figures.

FIG. 1 is a cross-section view of the surgical instrument of the invention.

FIG. 2 is an enlarged partial view of the distal end of the instrument shown in FIG. 1.

FIG. 3 is an enlarged partial view of the proximal end of the instrument shown in FIG. 1.

FIG. 4 is an enlarged cross-section view of the dual core optic fiber of the instrument of the invention.

FIG. 5 is an enlarged schematic representation of the proximal end of the dual core optic fiber.

FIGS. 6 and 7 are enlarged schematic representations of the distal ends of two different embodiments of the dual core optic fiber.

DETAILED DESCRIPTION OF THE PREFERRED EMBODIMENTS

The surgical instrument of the invention is intended to provide both illumination light and laser light in laser eye surgery. However, it should be understood that the instrument of the invention may be used in other types of surgical procedures and that the instrument of the invention may be combined with other types of surgical instruments, for example, instruments that provide aspiration to a surgical site, or with a bipolar cautery device, or other types of surgical devices. The instrument can be designed as a disposable instrument, and can also be designed as a reusable instrument that is sterilized after each use.

The instrument has an elongate, narrow handle or hand piece 12 that has opposite proximal 14 and distal 16 ends. The handle 12 is dimensioned to a size similar to that of a pencil, to fit comfortably in the surgeon's hand and to be easily manually manipulated by the surgeon. A hollow interior bore 18 extends completely through the center of the handle 12 from the proximal end 14 to the distal end 16. In an alternative embodiment, the handle could be provided with a groove in the side of the handle that extends along the length of the handle.

An elongate, tubular tip 22 projects from the handle distal end 16. The tip is rigid and is preferably constructed from surgical steel. The tubular tip 22 has a hollow interior bore 24 that extends completely through the tip from a proximal end 26 of the tip to a distal end 28 of the tip. The tip proximal end 26 is received in the handle interior bore 18 at the handle distal end 16 and is secured to the handle. The tip bore 24 communicates with the handle bore 18 and has a center axis 30 that is coaxial with a center axis of the handle. The tip 22 projects axially from the handle distal end 16 to the distal end 28 of the tip. In the alternate embodiments of the instrument, the tip 22 can be curved along a portion of its length. In addition, in alternate embodiments the tip could be flexible, and the tip could be mounted to the handle for reciprocating movements of the tip into and out of the handle interior bore 18. In such an embodiment, an actuator would be provided on the handle for manipulation by the user's hand. The actuator would be connected with the tip to cause movements of the tip relative to the handle in response to movements of the actuator on the handle.

A dual core optic fiber 32 extends through the handle bore 18 and the tip bore 24. The optic fiber 32 has an elongate length that extends from a proximal end 34 to a distal end 36 of the optic fiber. A majority of the optic fiber length is outside of the instrument handle 12 and the instrument tip 22. The majority of the optic fiber length being outside of the instrument handle 12 allows the optic fiber length to flex freely as the instrument handle 12 is manipulated during use of the instrument. In the illustrated embodiment, the optic fiber 32 is secured stationary relative to the handle 12 and the tip 22 by adhesives or other equivalent means. In alternate embodiments of the invention, the tubular tip 22 could be movable relative to the optic fiber 32, or the optic fiber 32 could be movable through the handle interior bore 18 and the tip interior bore 24.

A laser light source connector 38 is provided at the optic fiber proximal end 34. The connector 38 is a conventional connector that is adapted for connecting the optic fiber proximal end 34 to a separate light source, preferably a light source that delivers coaxially aligned laser light and white light illumination. There are many different available light sources that are used in microsurgery and in particular ophthalmic surgery, and the connector 38 can be altered so that the instrument of the invention may be used with any of these available light sources. The proximal end 34 of the optic fiber 32 extends completely through the connector 38 and an end surface of the optic fiber proximal end 34 is positioned in the same plane as the proximal end of the connector 38. The optic fiber 32 extends from the connector 38 through the handle interior bore 18 and the tip interior bore 24 to the distal end 36 of the optic fiber positioned adjacent the tip distal end 28. The light received by the optic fiber proximal end 34 travels through the length of the optic fiber 32 and is emitted from the optic fiber distal end 36.

A novel feature of the invention is provided by the dual core construction of the optic fiber 32. The optic fiber 32 has four basic components that extend along the length of the fiber. The components include a tubular outer core 42, an inner, center core 46 that extends through the outer core 42, a cladding layer 48 that surrounds the outer core 42, and a buffer layer 50 that surrounds the cladding layer 48. In the preferred embodiment of the invention, the components of the optic fiber are made as one piece. The center core 46 extends the entire length of the optic fiber from the proximal end 34 to the distal end 36. The outer core 42 surrounds the center core 46 and also extends from the optic fiber proximal end 34 to the distal end 36. The cladding layer 48 surrounds the outer core 42 and extends from the optic fiber proximal end 34 to the optic fiber distal end 36 in one embodiment, and to a position adjacent the distal end 36 in a further embodiment. The buffer layer 50 surrounds the cladding layer 48 and extends a majority of the length of the optic fiber from the connector 38 adjacent the proximal end 34 to the handle 12 adjacent the distal end 36. The two cores 42, 46 of the optic fiber are made of silica glass, each having a different index of refraction. Other materials that are capable of transmitting light may be used to construct the two cores 42, 46 other than silica glass. For example, the fibers could be constructed of a mixture of silica and plastic. Also, the inner core could be silica glass and the outer core could be plastic. In the dual core optic fiber 32, the outer core 42 functions as a first, illumination optic fiber that transmits illuminating light and the inner core 46 functions as a second, laser optic fiber that transmits laser light. In the preferred embodiment, the material of the first optic fiber 42 has a first index of refraction, and the material of the second optic fiber 46 has a second index of refraction. In the preferred embodiment where the second optic fiber 46 transmits laser light and the first optic fiber 42 transmits illumination light, the second index of refraction is larger than the first index of refraction. The outer core 42 has an index of refraction of 1.436 and the center core 46 has an index of refraction of 1.453 in the preferred embodiment. However, the index of refraction for the outer core could range between 1.26 and 1.59 and the index of refraction for the center core could range between 1.40 and 1.60.

The cladding layer 48 is made of a cladding material having a lower index of refraction than that of the outer core 42 and the center core 46. The cladding 48 has an index of refraction of 1.388 in the preferred embodiment, but the index of refraction could range between 1.25 and 1.40. The cladding could be constructed of silica glass or plastic or a mixture of both. Where the center core 46 and the outer core 42 transmit the light through the optic fiber 32, the cladding layer 48 keeps the light from exiting the dual cores. The cladding layer 48 works by having a lower refractive index from that of the dual cores 42, 46 such that, when the laser light hits the cladding layer 48 it is reflected back into the dual cores. Thus, the outer core 42 will always have an index of refraction between that of the inner core 46 and the cladding 48.

The buffer layer 50 protects the cladding layer 48 and the dual cores 42, 46 from damage.

The changes in the index of refraction between the center core 46, the outer core 42, and the cladding layer 48 give the center core 46 a lower Numerical Aperture (NA), and give the outer core 42 a much higher Numerical Aperture. This results in the center core 46 of the fiber only accepting light that has a narrow divergence angle, such as laser light, while the outer core 42 accepts light having a more divergent angle, such as the illuminating light from the source. This is depicted in FIG. 5 where the laser light 52 is shown entering the center core 46 and the illumination light 54 is shown entering the outer core 42 at the optic fiber proximal end 34. This relationship is also important at the optic fiber distal end 36 where the relationship is also true of the light leaving the optic fiber distal end.

The center core 46 of the optic fiber will emit light at both narrow and wide divergence angles. This happens because the wider divergence angle light rays refract through the center core 46 along the length of the optic fiber. The outer core 42 of the optic fiber will also emit narrow and wide angle light. The inner core 46 will maintain a narrow divergence angle light that impinges on the proximal end 32 of the center core 46, for example when the connector 38 is connected to a separate laser light source (not shown). Thus, if the laser light from the laser light source is focused only on the proximal end of the center core 46, the center core 46 will only emit laser light from the center core distal end 64.

The center core 46 will emit a light having a narrow divergence angle 56 where the outer core 42 will emit a light having a larger divergence angle 58. FIG. 6 represents the laser light 56 and illumination light 58 emitted from the optic fiber distal end 56 where the distal end surface is normal to the center axis of the optic fiber. FIG. 7 represents the effective divergence angle of the outer core 42 being increased by tapering the distal end tip at the outer core 42, while leaving the distal end surface of the center core 46 normal to the optic fiber center axis. The tapered surface, preferably a beveled surface 62 at the distal end of the outer core 42 helps scatter the illumination light away from the optic fiber center axis 30, while the normal surface 64 at the distal end of the center core 46 remains unaffected. Other light diverging optics could be used at the distal end of the outer core 42 instead of the tapered surface 62. For best results the light emitted from the outer core 42 is given as high a Numerical Aperture as possible.

Thus, as discussed above, the surgical instrument of the invention provides a single microsurgical instrument that delivers both laser light and illumination light from a single instrument and from a single light source.

Although specific embodiments of the invention have been described herein, it should be understood that other modifications and variations may be made to the invention without departing from the protected concept of the invention.

The invention claimed is:

1. A surgical instrument that provides light to a surgical site, the instrument comprising:
    a handle that is dimensioned to be held in a hand and manually manipulated;
    a tubular tip mounted on the handle and projecting from the handle to a distal end of the tip, the tip having an interior bore that extends through the tip to the tip distal end;
    a first optic fiber, the first optic fiber having a length that extends between opposite proximal and distal ends of the first optic fiber, the first optic fiber extending through the tip interior bore to the first optic fiber distal end positioned adjacent the tip distal end; and,
    a second optic fiber, the second optic fiber having a length with opposite proximal and distal ends, the second optic fiber extending through the first optic fiber to the distal end of the second optic fiber positioned adjacent the distal end of the first optic fiber.

2. The instrument of claim 1, further comprising:
    the first and second optic fibers having a common center axis at the optic fiber distal ends; and,
    the optic fibers having light diverging optics at the optic fiber distal ends that diverge light transmitted from the optic fiber distal ends away from the optic fibers center axis.

3. The instrument of claim 2, further comprising:
    the light diverging optics being a tapered surface on at least one of the optic fiber distal ends.

4. The instrument of claim 3, further comprising:
    the tapered surface being a conical surface.

5. The instrument of claim 1, further comprising:
    the optic fibers being secured stationary relative to the handle.

6. The instrument of claim 1, further comprising:
    the tubular tip being a rigid tip that projects straight from the handle.

7. The instrument of claim 1, further comprising:
    the optic fibers being constructed of silica glass.

8. The instrument of claim 1, further comprising:
    the first optic fiber being an illumination optic fiber that transmits illumination light and the second optic fiber being a laser optic fiber that transmits laser light.

9. The instrument of claim 1, further comprising:
    a connector on both the first optic fiber proximal end and on the second optic fiber proximal end, the connector being adapted for connecting the first optic fiber proximal end and the second optic fiber proximal end to a light source.

10. The instrument of claim 1, further comprising:
    the second optic fiber extending through the first optic fiber from the first optic fiber proximal end to the first optic fiber distal end.

11. The instrument of claim 1, further comprising:
    the first optic fiber having a center axis at the first optic fiber distal end, and the first optic fiber having light diverging optics at the first optic fiber distal end that diverge light transmitted from the first optic fiber distal end away from the center axis.

12. The instrument of claim 11, further comprising:
the light diverging optics being a tapered surface on the first optic fiber distal end.

13. The instrument of claim 12, further comprising:
the second optic fiber having a distal end surface positioned in a plane that is perpendicular to the first optic fiber center axis.

14. The instrument of claim 1, further comprising:
the first optic fiber having a first index of refraction and the second optic fiber having a second index of refraction that is different from the first index of refraction.

15. The instrument of claim 14, further comprising:
the first index of refraction being smaller than the second index of refraction.

16. A surgical instrument that provides light to a surgical site, the instrument comprising:
a handle that is dimensioned to be manually manipulated;
a tubular tip mounted on the handle and projecting from the handle to a distal end of the tip, the tip having a hollow interior bore extending through the tip from the handle to the tip distal end;
a first illumination light transmitting optic fiber having a length with opposite proximal and distal ends, the first optic fiber extending through the tip interior bore to the distal end of the first optic fiber positioned adjacent the tip distal end; and,
a second laser light transmitting optic fiber having a length with opposite proximal and distal ends, the second optic fiber extending through the first optic fiber to the distal end of the second optic fiber positioned adjacent the distal end of the first optic fiber.

17. The instrument of claim 16, further comprising:
the first optic fiber and the second optic fiber having a common center axis at the distal ends of the first optic fiber and the second optic fiber; and,
the first optic fiber having light diverging optics at the distal end of the first optic fiber that diverge illumination light transmitted from the first optic fiber distal end away from the center axis.

18. The instrument of claim 17, further comprising:
the light diverging optics on the first optic fiber distal end being a tapered surface on the first optic fiber distal end.

19. The instrument of claim 18, further comprising:
the second optic fiber having a distal end surface positioned in a plane that is perpendicular to the center axis.

20. The instrument of claim 16, further comprising:
the first optic fiber and the second optic fiber being secured stationary relative to the handle.

21. The instrument of claim 16, further comprising:
the tuber tip being a rigid tip that projects straight from the handle.

22. The instrument of claim 16, further comprising:
the first optic fiber having a first index of refraction; and,
the second optic fiber having a second index of refraction that is different from the first index of refraction.

23. The instrument of claim 16, further comprising:
a connector on the first optic fiber proximal end and on the second optic fiber proximal end, the connector being adapted for connecting the first optic fiber proximal end and the second optic fiber proximal end to a light source.

24. A surgical instrument that provides light to a surgical site, the instrument comprising:
a manually manipulable handle;
a tubular tip secured to the handle, the tip projecting from the handle to a distal end of the tip;
a first illumination light transmitting optic fiber having a length with opposite proximal and distal ends, the first illumination optic fiber extending through the handle and through the tip to the first illumination optic fiber distal end positioned adjacent the tip distal end;
a second laser light transmitting optic fiber having a length with opposite proximal and distal ends, the second laser optic fiber extending through a center of the first illumination optic fiber, the second laser optic fiber extending through the center of the first illumination optic fiber from the proximal end of the first illumination optic fiber to the distal end of the first illumination optic fiber;
the second laser optic fiber having an index of refraction and the first illumination optic fiber having an index of refraction, the second laser optic fiber index of refraction being larger than the first illumination optic fiber index of refraction.

25. The instrument of claim 24, further comprising:
the first optic fiber and the second optic fiber having a common center axis at the distal ends of the first optic fiber and the second optic fiber; and,
the first optic fiber having light diverging optics at the distal end of the first optic fiber that diverge light transmitted from the first optic fiber distal end away from the center axis.

26. The instrument of claim 25, further comprising:
the light diverging optics on the first optic fiber distal end being a tapered surface on the first optic fiber distal end.

27. The instrument of claim 26, further comprising:
the second optic fiber having a distal end surface positioned in a plane that is perpendicular to the center axis.

28. The instrument of claim 24, further comprising:
the first optic fiber and the second optic fiber being secured stationary relative to the handle.

29. The instrument of claim 24, further comprising:
the tip being a rigid tip that projects straight from the handle.

30. The instrument of claim 24, further comprising:
the first optic fiber being constructed of silica glass; and,
the second optic fiber being constructed of silica glass.

31. The instrument of claim 24, further comprising:
a connector on the first optic fiber proximal end and on the second optic fiber proximal end, the connector being adapted for connecting the first optic fiber proximal end and the second optic fiber proximal end to a light source.

* * * * *